US010939821B2

(12) United States Patent
Yaghi et al.

(10) Patent No.: US 10,939,821 B2
(45) Date of Patent: Mar. 9, 2021

(54) SYSTEMS AND METHODS FOR DIAGNOSING AND ANALYZING CONCUSSIONS

(71) Applicant: Applications Technology (AppTek), LLC, McLean, VA (US)

(72) Inventors: Mudar Yaghi, McLean, VA (US); Yasar Yaghi, Washington, DC (US); Darius Ferdows, Bethesda, MD (US); Jintao Jiang, Great Falls, VA (US)

(73) Assignee: Applications Technology (AppTek), LLC, McLean, VA (US)

( * ) Notice: Subject to any disclaimer, the term of this patent is extended or adjusted under 35 U.S.C. 154(b) by 126 days.

(21) Appl. No.: 15/926,820

(22) Filed: Mar. 20, 2018

(65) Prior Publication Data

US 2018/0263496 A1 Sep. 20, 2018

Related U.S. Application Data

(60) Provisional application No. 62/473,919, filed on Mar. 20, 2017.

(51) Int. Cl.
*A61B 5/103* (2006.01)
*A61B 5/00* (2006.01)
(Continued)

(52) U.S. Cl.
CPC .......... *A61B 5/0022* (2013.01); *A61B 5/1124* (2013.01); *A61B 5/162* (2013.01);
(Continued)

(58) Field of Classification Search
CPC ... A61B 5/0002; A61B 5/0004; A61B 5/0015; A61B 5/0022; A61B 5/103; A61B 5/11;
(Continued)

(56) References Cited

U.S. PATENT DOCUMENTS 10,342,473 B1* 7/2019 Berme .................. A61B 5/1114
2012/0330178 A1* 12/2012 Kraft .................. A61B 5/04842
600/544

(Continued)

*Primary Examiner* — Ahmed M Farah
(74) *Attorney, Agent, or Firm* — Morgan, Lewis & Bockius LLP; Robert C. Bertin; Rachael Lea Leventhal

(57) ABSTRACT

A mobile device is programmed with an application that uses the mobile device's camera, accelerometer and microphone to enable a parent, coach or player to use it as a tool to diagnose a concussion. The tool may diagnose concussion on the basis of one or multiple factors that are scored, for example the player's balance, eye movement, speech responses to questions, button pressing response time, and other information about the location of the impact. A mobile device may be equipped with speech recognition and voice prompting to enable a concussion examination of a player to be administered by another player or coach to the injured player without significant effort by the injured player or helper. Each test may be scored, by itself or against one or more baselines for the injured player to develop an overall score and likelihood of a concussion. When the coach thinks there is a concussion, he/she can use the application to help find a doctor. When the coach is not sure about the test results, he/she can send the machine learning annotated data to an online doctor for reviewing.

3 Claims, 10 Drawing Sheets

(51) Int. Cl.
*A61B 5/16* (2006.01)
*A61B 5/11* (2006.01)

(52) U.S. Cl.
CPC ............ *A61B 5/163* (2017.08); *A61B 5/4064* (2013.01); *A61B 5/4803* (2013.01); *A61B 5/6898* (2013.01); *A61B 5/7445* (2013.01)

(58) Field of Classification Search
CPC ... A61B 5/1101; A61B 5/1103; A61B 5/1124; A61B 5/1126; A61B 5/1128; A61B 5/16; A61B 5/162; A61B 5/163; A61B 5/15; A61B 5/40; A61B 5/4005; A61B 5/4023; A61B 5/4064; A61B 5/4058; A61B 5/4076; A61B 5/48; A61B 5/4803; A61B 5/6898
USPC .......................... 600/301, 544, 545, 558, 559
See application file for complete search history.

(56) References Cited

U.S. PATENT DOCUMENTS

| | | | |
|---|---|---|---|
| 2015/0040685 A1* | 2/2015 | Nicholson | G01L 1/2206 73/862.51 |
| 2016/0220167 A1* | 8/2016 | Allen | A61B 5/4064 |
| 2017/0258390 A1* | 9/2017 | Howard | A61B 5/16 |
| 2018/0168500 A1* | 6/2018 | Baleen | A61B 5/7278 |
| 2018/0322961 A1* | 11/2018 | Kim | A61B 5/4803 |
| 2019/0038167 A1* | 2/2019 | Jones | A61B 5/04012 |
| 2019/0380875 A1* | 12/2019 | Esmonde | A61B 3/113 |

\* cited by examiner

SYSTEMS AND METHODS FOR DIAGNOSING AND ANALYZING CONCUSSIONS

FIELD OF THE INVENTION

The present invention relates to diagnosing head trauma, and more particularly, to diagnosing head trauma using a mobile device based on the interaction of an injured user with features of the mobile device.

BACKGROUND OF THE INVENTION

It is well known that contact and other sports have the potential to produce concussions in players resulting from collisions with other players, equipment or the ground. This potential has resulted in various forms of in-office concussion testing and baseline testing using external equipment. Usually, a concussion baseline test needs to be scheduled for a specific time and in a specific location. When a player, particularly a young player has undergone a head trauma on a playing field, the player is typically far from a doctor and the player's coach is typically the first responder. The coach may or may not have received concussion training and in most events is not well equipped to diagnose the injury to the player.

There is a need for better and more convenient techniques for baseline tests and for identifying concussion signs and symptoms that can be captured by people who are nearby sports teams. There is a further need for concussion diagnosis to be made in a more accurate way based on equipment that is readily available. Given the convenience of the tests, the test can be administered by the coach, parents, and the player himself/herself. Therefore, more data will be captured and analyzed using machine learning techniques, and this will in turn make the system to provide better artificial intelligence, more accurate scores, and better annotated data for doctor's evaluation. This application can also help evaluate and track the progress of a concussion. In addition, the application's messaging system will connect the injured player with available doctors. When there is concussion, the application can help find an available doctor. When the coach is not sure about the test result, he/she can send the annotate data to an available doctor to review through the internet.

If a concussion does occur, the doctor or the coach can mark the case using the App so that it registers with the backend server. Then, the backend server has a collection of data on the baseline test and the test before/around the concussion. This type of data is very useful for repeated-measure analyses to find out important factors that might relate to concussion. For example, speech analyses and machine learning can produce a lot of features but we don't know which ones are useful in advance. Using data analyses and machine learning, we can optimize the scoring and add new features to the scoring and further improve the accuracy. After removing personal identifiable information, the data can be shared with scientific community and medical research institutes.

SUMMARY OF THE INVENTION

According to an embodiments of the present invention, a mobile device, such as a parent's, coach's or player's mobile phone is converted into a concussion diagnostic tool. The tool may diagnose concussion on the basis of one or multiple factors that are scored, for example the player's balance, eye movement, speech responses to questions, button pressing response time, and other information about the location of the impact. A mobile device may be equipped with speech recognition and voice prompting to enable a concussion examination of a player to be administered by another player or coach to the injured player without significant effort by the injured player or helper. Each test may be scored, by itself or against one or more baselines for the injured player to develop an overall score and likelihood of a concussion. The data captured by the mobile device may be sent to a backend server for processing and analyses using the state-of-the-art machine learning technologies. The analyzed/annotated data may be saved in the cloud for later review and analyses. When the coach thinks there is a concussion, he/she can use the application to help find a doctor. When the coach is not sure about the test results, he/she can send the machine learning annotated data to an online doctor for reviewing.

According to another embodiment, the examiner administers a comprehensive set of tests using a mobile device. The athlete user responds to the tests by using speech (for cognitive tests), by pressing buttons on mobile device (for response time test), by following a moving mobile device (for eye tracking), and hold the mobile device and move under the examiner's direction (for balance tests). For all the tests, the mobile device will capture the data (speech, response delays, eye video, and accelerometer data) and send to a backend server for analyses and scoring using machine learning approaches. The scores will be computed in relation to a baseline and are indicative of likelihood of concussion. After the analyses, the annotated data will be saved on the cloud server for doctor's review and for a trend analysis. The speech analyses include speech recognition, natural language processing, slurring, pitch analysis, phoneme alignment, hesitation analysis, speech delay, spectrum analysis, speaker identification and comparison, etc. The response time analyses include mean, medium, variance, and slope. The eye tracking analyses will include image analysis, eye tracking, eye gaze estimation, eye movement classification, estimating fixation stability and smooth pursuit lag. The application also has a function to help find available concussion doctors. This invention is different from other existing systems as it includes the state-of-the-art artificial intelligence and machine learning technologies, it works on a mobile device, and it includes back-end servers for analyzing and data storage. Thus, this invention produces a more accurate, timely, and convenient way of assessing brain injuries given such a variety of tests/assessments. Also, an important aspect of the App is that it can provide an abundant of data for scientific research and for self-improving using machine learning.

BRIEF DESCRIPTION OF THE FIGURES

The above described features and advantages of the invention, will be more fully appreciated with reference to the attached drawing figures.

DETAILED DESCRIPTION

Figure 1:
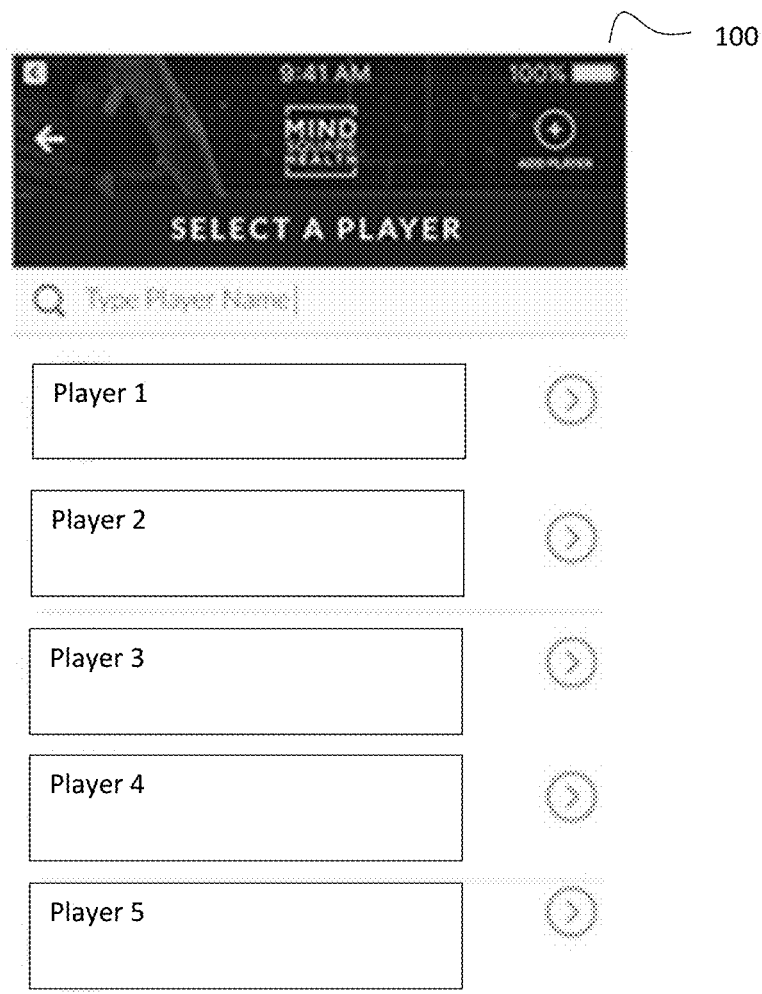
FIG. 1 depicts a view of a mobile device's screen while displaying a concussion application that allows a user to select a player for concussion testing.

According to one or more embodiments of the present invention, a mobile device, such as a parent's, coach's or player's mobile phone is converted into a concussion diagnostic tool. The tool may diagnose concussion on the basis of one or multiple factors that are scored, for example the player's balance, eye movement, speech responses to questions, button pressing response time, and other information about the location of the impact. A mobile device may be equipped with speech recognition and voice prompting to enable a concussion examination of a player to be administered by another player or coach to the injured player without significant effort by the injured player or helper. Each test may be scored, by itself or against one or more baselines for the injured player to develop an overall score and likelihood of a concussion. The data captured by the mobile device may be sent to a backend server for processing and analyses using the state-of-the-art machine learning technologies. The analyzed/annotated data may be saved in the cloud for later review and analyses. When the coach thinks there is a concussion, he/she can use the application to help find a doctor. When the coach is not sure about the test results, he/she can send the machine learning annotated data to an online doctor for reviewing.

According to another embodiment, the examiner administers a comprehensive set of tests using a mobile device. The athlete user responds to the tests by using speech (for cognitive tests), by pressing buttons on mobile device (for response time test), by following a moving mobile device (for eye tracking), and hold the mobile device and move under the examiner's direction (for balance tests). For all the tests, the mobile device will capture the data (speech, response delays, eye video, and accelerometer data) and send to a backend server for analyses and scoring using machine learning approaches. The scores will be computed in relation to a baseline and are indicative of likelihood of concussion. After the analyses, the annotated data will be saved on the cloud server for doctor's review and for a trend analysis. The speech analyses include speech recognition, natural language processing, slurring, pitch analysis, phoneme alignment, hesitation analysis, speech delay, spectrum analysis, speaker identification and comparison, etc. The response time analyses include mean, medium, variance, and slope. The eye tracking analyses will include image analysis, eye tracking, eye gaze estimation, eye movement classification, estimating fixation stability and smooth pursuit lag. The application also has a function to help find available concussion doctors. This invention is different from other existing systems as it includes the state-of-the-art artificial intelligence and machine learning technologies, it works on a mobile device, and it includes back-end servers for analyzing and data storage. Thus, this invention produces a more accurate, timely, and convenient way of assessing brain injuries given such a variety of tests/assessments. Also, an important aspect of the App is that it can provide an abundant of data for scientific research and for self-improving using machine learning.

A mobile App may be used according to some embodiments of the invention. The App may be distributed for example in Apple App Store or in Google Play or otherwise made available or distributed for use on mobile devices, like mobile phones, tables or laptops, or other computing devices.

The App may have a user account management that communicates with a backend server. A player can have his/her own account. In this account, the player can perform a self-evaluation, review his/her annotated past test data and results, perform a trend analysis, review statistics in the region/group, and message his/her coach. The coach has an account that manages a list of players. A player can ask to join a coach, and a coach can invite a player to join. The coach can use his/her account to administer a test. The coach can also review annotated test results in the past. Tests are labeled as self-initiated, parent-initiated, and coach-initiated. Parents also can have accounts.

The App users can login to their accounts in a traditional way (typing in username and password) or choose to use voice authentication. After the login, the user can choose to operate through buttons or through voice. The voice will be streamed to a backend server for speech recognition and natural language understanding. The speech will be converting to actions. For example, an examiner could register a player but dictating all the details: "John is 5'11, 190 lbs, male, running back. Take me to the eye-tracking test". The app would register all these details and launch the eye tracking test.

Before the test, the trainer can also input some information about the player. But this is optional. Again, the trainer can type in the information or use voice interface. The information can include the helmet make and model, the condition of the player (having a cold, having a fever, or headache).

The App has user interface for the tests. There are many pages for the tests. Once a test is selected, the App will collect data (audio, video, button press time, accelerometer), communicate with a backend/cloud server, and display results. The App may display a warning if the recognized speaker identity is different from the registered user.

In the App, there is an option for a coach to choose to administer the test using button pressing or using speech recognition.

The message also has a messaging system between coach, player, and doctors. The doctor or the coach can mark a concussion test if a concussion does occur. Referring to FIG. 1, the mobile device 100 may have a screen display associated with each team that lets a coach, player, parent, trainer or other person select a player on each team on which to perform a concussion baseline test or perform a concussion test.

The mobile device may be a mobile phone, table, laptop computer or any other type of computer. The mobile device typically includes at least one processor coupled with a memory, input/output device such as a display or touchscreen display or keys, at least one network connection such as a wireless (wi-fi, bluetooth and/or cellular network connection) or other network connection, a microphone, speaker, headphones (wireless or wired) and other devices that are included in a mobile phone such as an accelerometer for inertial measurement and measurement of the position and angle of the phone, steps, sway, etc., GPS, and other devices. The processor executes program instructions for an operating system and application programs that enable the mobile device to access each of its systems and interact with a user through the input out system and collect images, audio, video and other data from sensor and send such data to the back end processing server for concussion analysis in accordance with embodiments of the invention. The application programs and program instructions may implement the steps and processes shown below in connection with the concussion application.

The back end processing server includes a network connection and the ability to receive and analyze data from the mobile device and may include all or portions of the hardware and functionality described above in connection with the mobile device. The analysis is performed by a processor executing program instructions that may execute the functionality shown and described in the figures below as associated with the back end processing server.

Tests

The mobile application is broken into the following assessments, which may be done anywhere but are preferably all done through a mobile device close to where an incident occurred or at least close to the user who uses the app for baseline, self-diagnosis or facilitated diagnosis by a parent, coach, trainer or other helper.

Cognitive Assessment

According to some embodiments, the trainer will have the athlete wear bluetooth earphones [if outside environment is too loud] to listen to 15 questions (see appendix I for list of questions). The trainer can either say "Question 1" or press a button to go to the first question, which will be played to the player. When the player speaks in reply to each question, the audio will be streamed to a backend server for voice activity detection (VAD), speech recognition (e.g., "february second two thousand seventeen"), natural language processing (e.g., "2/2/2017"), and other speech analyses. Then the App will display the results (recognized text and whether it is correct).

The App will prompt the trainer to the next step (moving on to the next question, re-doing the question, and instructing the player how to answer). For each question, the answer is streamed to the back and server and additional processing will be running on the backend server to analyze the pitch (tone), delay in the response, speed of speech, clarity of the speech, hesitation in the speech (uh-uh), and phoneme duration, and speaker identification (SID). The app or back end processing associated with the app or otherwise analyzes for pitch, delay, speed, and hesitation among other factors in some embodiments. For the pitch analysis, we will analyze for changes in the pitch and if there is any trembling in pitch. For the delay in response, we will look at how long it takes for the player to start answering. For the speed of speech, we will look at how long the speech is. For the clarity of the speech, we will look into the confidence in the recognition results. We will also detect the hesitation filler in the speech (uh-uh). For the phoneme duration analysis, we will look into any change in the phoneme patterns (some phonemes might be omitted due to concussion). For the SID, we will evaluate whether the player sounds like a different person.

When all the questions are answered, we will summarize and present at least one score. According to some embodiments, a general score is generated as indicative of likelihood of concussion based on the analyzed speed as described above. The score may also be based on two baseline numbers: One is universal baseline for which we will use crowd-sourcing (e.g., Mechanical-Turk) to collect a general based data; and the other is individual baseline for which each individual will perform baseline tests. For the universal baseline test, each individual will perform the tests several times spanning a few days. In this way, we can compute the intra-person and inter-person differences. The universal baseline will provide a general distribution of features in terms of gender, age group, language background, weight, and height. The individual baseline will provide a reference for that individual. For example, if the system detects a pitch change, it will generate a significance score for such change. The higher the significance, the higher the possibility of concussion. In the end, all the factor scores will be weighted to produce an overall concussion score.

TABLE 1

Questions for the Cognitive Assessment

1. What is the current year?
2. What is the current month?
3. What is the current day?
4. What is the current date?
5. What is the current time?
6. Repeat the following words: radio, cloud, scorecard, table, nickel.
7. Repeat these numbers: 28541?
8. Repeat 17362 in reverse order?
9. Subtract 6 from 99 three times?
10. Spell the word SPORTS backwards?
11. Say the words of the week backwards?
12. Put the letters from the word "WIN" in backwards order.
13. Put the letters from the word "PLAY" in backwards order.
14. Put the letters from the word "TEAMS" in backwards order.
15. You were asked to repeat five words at the beginning. Which words do you remember?

Figure 2:
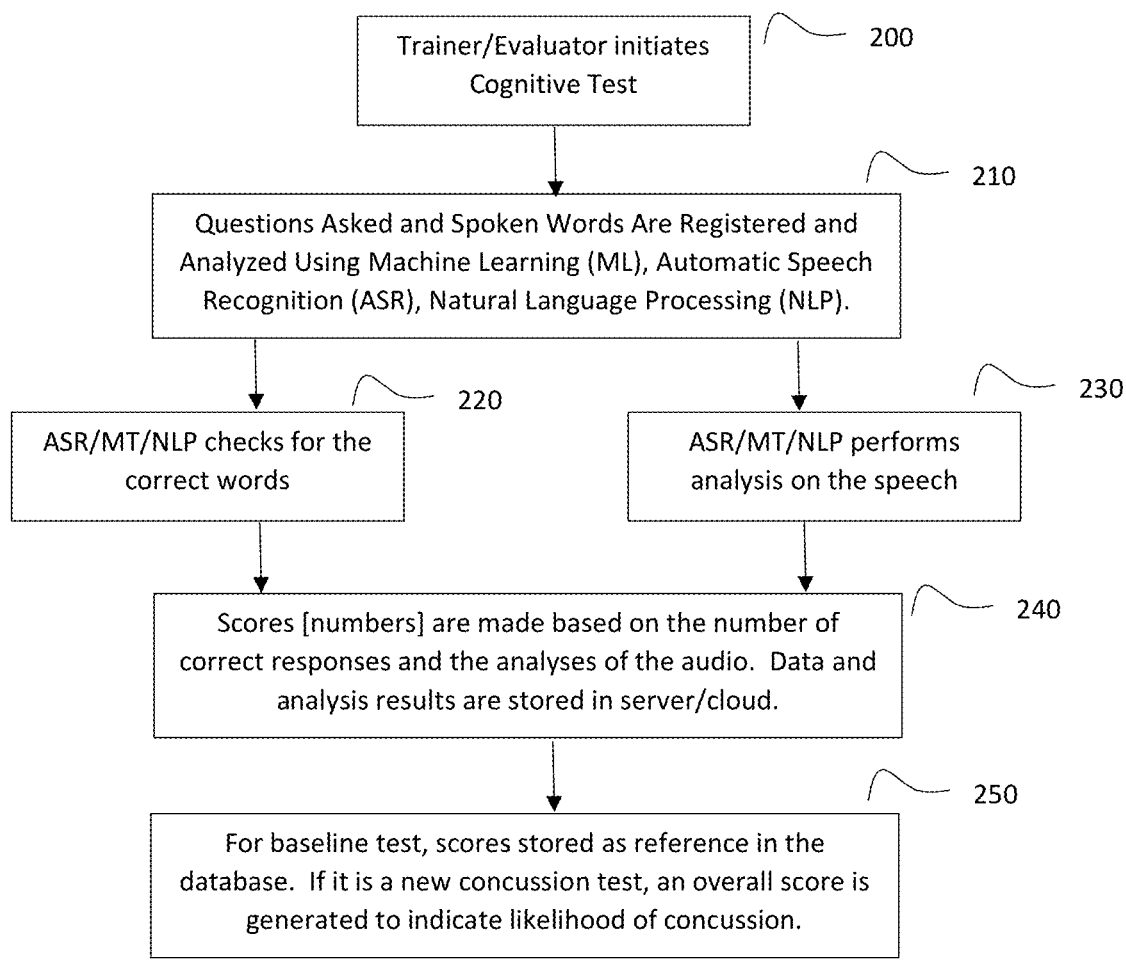
FIG. 2 depicts a method for determining a baseline score and concussion test based on questions and responses, according to an embodiment of the invention.

FIG. 2 depicts a method of performing a cognitive test using a mobile device with application software and a back end server with software as described herein according to one embodiment of the invention. Referring to FIG. 2, in step 200 a cognitive test is initiated by an evaluator, which may be a player, user, coach, parent teacher or other party. In step 210, questions are asked and answered. Table 1 may be used as an illustrative source of questions for the method. For example, Questions 6-8 and 15 can serve as a memory and attention test. For Question 6, the five words (radio, cloud, scorecard, table, nickel) will be randomized in order first and then be presented to the player using text-to-speech (TTS) technology. The player will need to repeat these words in order that they are heard. The speech recognition technology will register all correct words. For Question 7, five numbers from 1-9 will be selected and randomized in order first and then be presented to the player. The player will need to repeat these numbers in order that they are heard. For Question 8, five numbers from 1-9 will be selected and randomized in order and then be presented to the player. The player will need to order these numbers from the smallest to the largest. The Questions 6-8 may be repeated two-three times. The Questions 9 and 11 can serve to test the player's analytic ability. For Question 9, a random number A from 80 to 99 will be chosen, and a random number B will be chosen from 5 to 9. The player will be asked to subtract B from A three times. For example, the App may prompt "Please subtract 6 from 99 three times." This question may be repeated two-three times. For Question 11, the player will instruct to say the weekdays backwards starting with Sunday or Wednesday.

The Questions 10 and 12-14 can function as attention and memory tests as well. For these questions, four-letter or five-letter popular and regular words will be randomly chosen from a list (e.g., sport, teams, week, food, game) and be presented to the player. The player will be ask spell backwards. Questions may be taken from table 1 or 2 in some embodiments and used in whole or in part in some embodiments or combined with each other.

In step 220, automatic speech recognition (ASR) may be used to check for the correct words. In step 230, ASR, machine translation (MT) and/or natural language processing (NLP) may be used to perform analysis on the speech. Analysis may include the duration of a word, which may reflect slurring and other data on the degree of matching of utterances to prior utterances by the same concussion suspect in the baseline or after a prior concussion. In step 240, according to the method, the processor running the concussion software determines a score based on the number of correct responses and the analyses of the audio. The data analysis and results are stored on a server associated with the concussion application. In 250, for baseline testing, the scores and analyses are stored in a database as a baseline test, which may later be used to test the corresponding user for a concussion. New tests test the likelihood of a concussion and information and analyses for these tests are also stored.

Figure 3:
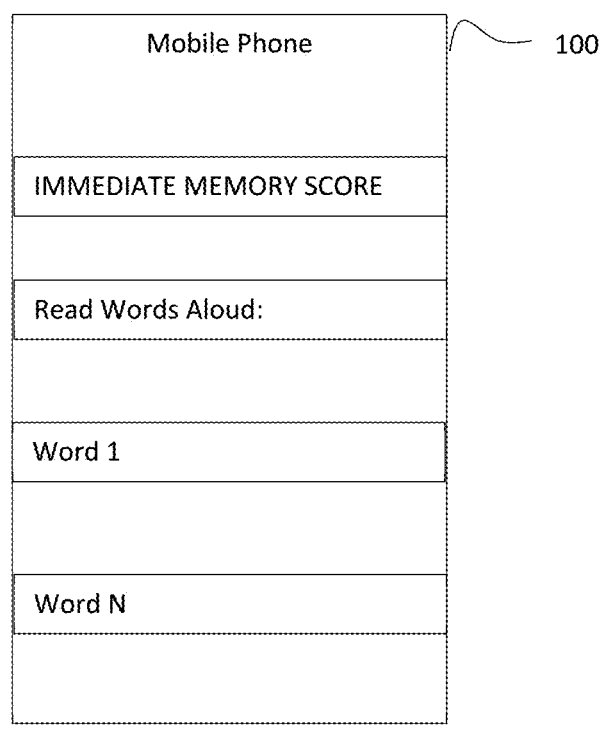
FIG. 3 depicts a view of a mobile device that prompts a user for a reading analysis test.

FIG. 3 depicts a display of a mobile phone that illustrates an application to test memory and utterance. Words, such as those identified herein, may be required to be memorized, read aloud and then analyzed.

Eye Tracking Assessment:

For an eye tracking assessment using the mobile device, the trainer will first press a button to play the instruction to the player so that the player will look at the back of the mobile device and focus on the camera lens when the while the trainer moves the mobile device moves from right to left, up and down in an 'H' pattern. After the instruction, the trainer will press a button to start the eye tracking test and to turn on the camera. The trainer will then move the mobile device in the 'H' pattern. The images will be streamed to a backend server for analyses. Note that the streaming rate will be 8 fps to reduce data. Through eye tracking technologies (facial recognition) and the accelerometer of the mobile device, the movement of the athlete's iris/pupil will be measured and quantified by these technologies. For example, the system will find the locations of eyes, iris/pupils, nose, and mouth in each image and then track the location across images. Based on these estimates, the system estimates the distance of face and its angle in relation to the camera and ultimately the fixation point of eyes. Consequently, eye fixation stability and smooth pursuit lag can be estimated. These data will be compared against the universal baseline and the individual baseline to generate an estimated score of likelihood of concussion. At the same time, this score will be later weighted and combined to estimate the overall concussion score.

Figure 4:
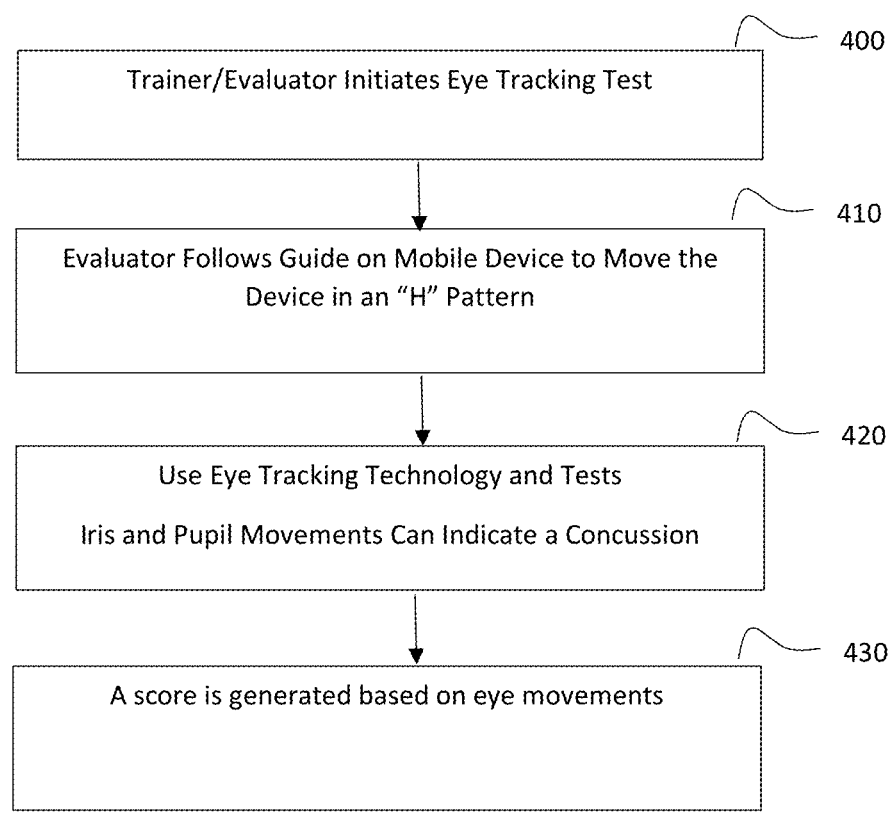
FIG. 4 depicts a method for performing an eye tracking test according to an embodiment of the present invention.

Referring to FIG. 4, an evaluator conducts an eye tracking test. Referring to FIG. 4, in step 400, the trainer/Evaluator initiates an eye tracking test using the app. In 410, the evaluator follows guide on the mobile device 100 to move the device in an "H" pattern. In 420, the mobile phone uses imaging processing technology to locate the concussion suspects eyes, pupils and irises and analyzes iris and pupil movements, which may indicate a concussion. In 430, the application calculates a score based on the eye movements.

Eye Movement Test

Figure 5:
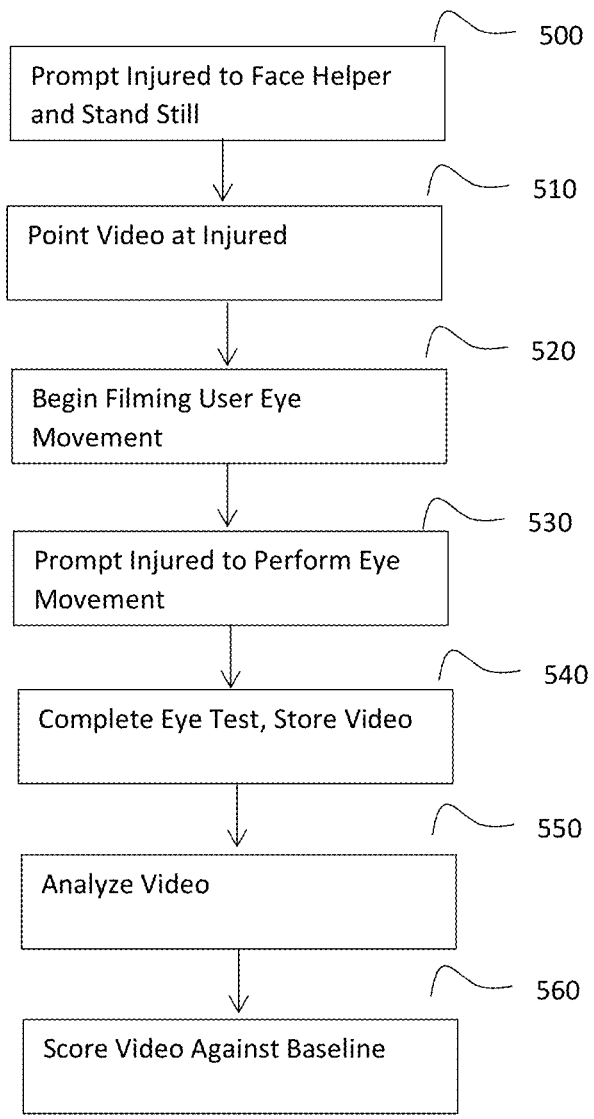
FIG. 5 depicts a method for determining a score during a balance test.

Referring to FIG. 5, another method of performing an eye movement test is described below. In 500, the injured is prompted to face the helper and stand still. In 510, the camera from the mobile device 100 is pointed at the injured. In 520, the camera operator films the injured making eye movements. In 530, the injured is prompted to perform "H" eye movements while being filmed by the mobile device 100. In 540, the complete eye test is stored in the server and the eye positions and movement of the iris and pupils are included. In 550, the video is analyzed and in 560, a score is determined, which may become a baseline if it is the first test or may be an actual concussion test if later.

Figure 6:
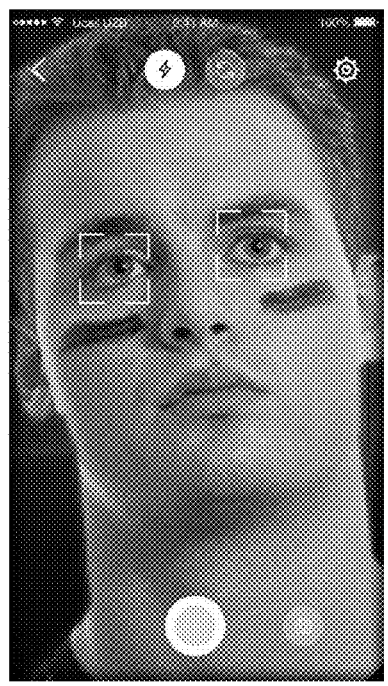
FIG. 6 depicts an application photograph that illustrates using facial features to facilitate testing, including balance testing.

The image in FIG. 6 for mobile device 100 highlights that facial recognition technology on the mobile device may be used to recognize faces, eyes, pupil location and face angle and other information. This technology may be then used as described above to analyze and ultimately score eye tracking movement.

Balance Test:

This test can be done in two ways:

First, an athlete will hold mobile device to their chest and perform a series of balancing maneuvers, standing on one leg and walking in a straight line similar to a DUI police test. The mobile device's accelerometer will measure the level of balance. Using the accelerometer in the mobile device a score will be generate to determine how well the athlete did. The trainer will initiate each test by pressing a button. The accelerometer data will be sent to the backend server for analyses and compared to universal baseline and individual baseline. In these tests, the analyses include speed stability and direction stability.

The tests from above will be video taped. Using video analysis and setting certain parameters, the athlete should be within these ranges.

Figure 9:
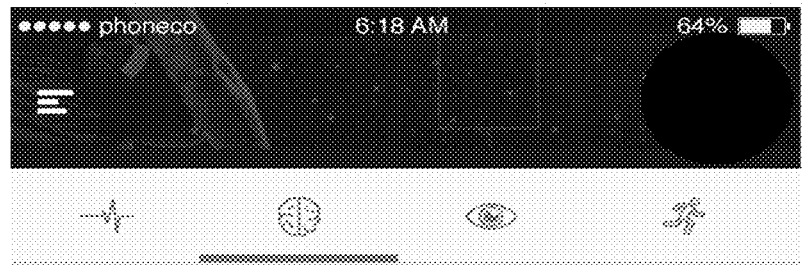
FIG. 9 depicts a sway test.
Figure 9:
Figure 9:
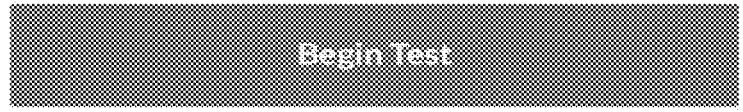

Second, an athlete can be recorded by video doing a sway test (as shown in FIG. 9) or performing any of the balancing tests described above, which may then be subject to video analysis as described herein.

Figure 7:
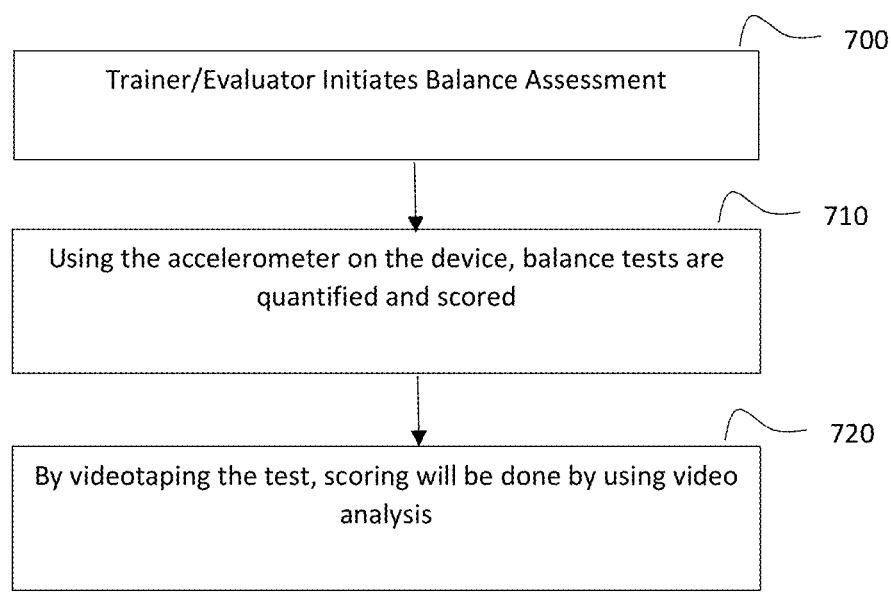
FIG. 7 depicts a balance test method.

Referring to FIG. 7, in 700 a trainer initiates a balance assessment on an injured using the mobile device 100. In 710, using the accelerometer on the mobile device, balance tests are conducted as described herein. The balance tests are then analyzed using the data from the accelerometer to determine wobble, falling and other deviations from good balance and score the balance test on the basis of the measurements. In 720, scoring is done using video analysis, relying on images of the location of a user's limbs and body. The video and accelerometer scores may be completely independent or may be combined.

Figure 8:
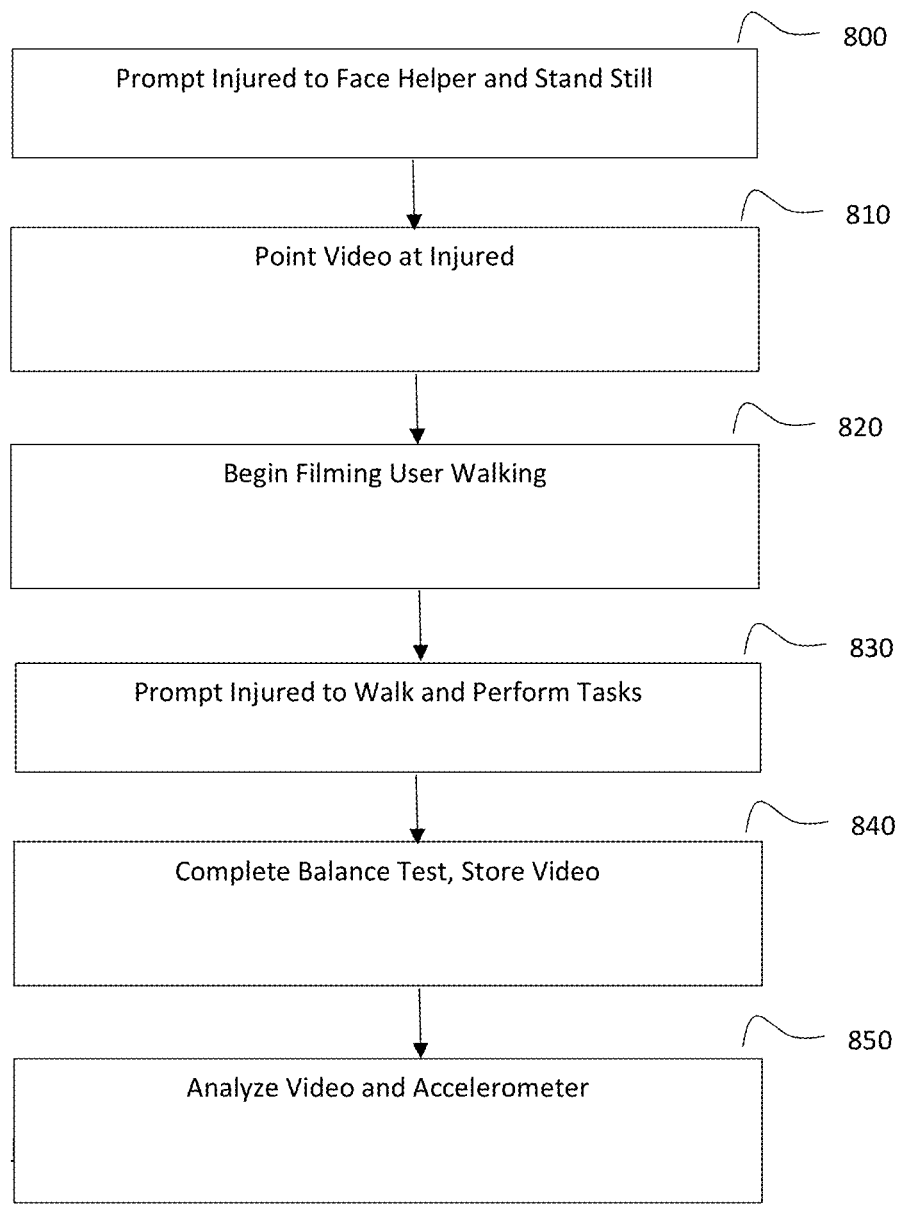
FIG. 8 depicts another balance test method.

FIG. 8 depicts another method of performing a balance test using the mobile device 100. Referring to FIG. 8, in 800, an injured is prompted to face a helper and stand still. In 810, the mobile device is pointed a the injured. In 820, the mobile device begins filming a user walking. In 830, the injured is prompted to walk and perform tasks. In 840, the balance test is completed and the video stored on the server along with the accelerometer recordings. In 850, the mobile device analyzes the video of the subject and the accelerometer to determine deviations from balance that occur during the balancing test and to assign as score as a result.

Reaction Test

Figure 10:
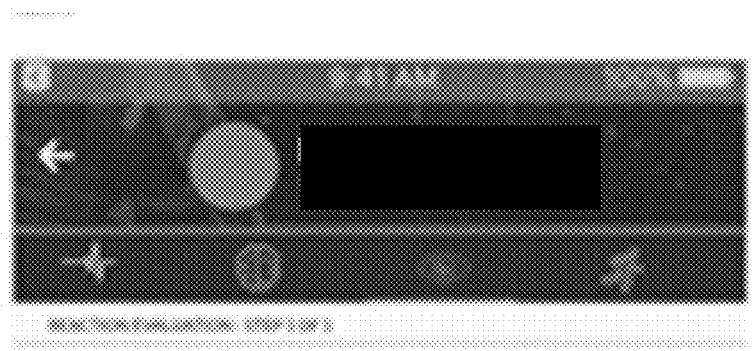
FIG. 10 depicts the application software on the mobile device running a listening test.
Figure 10:
Figure 10:
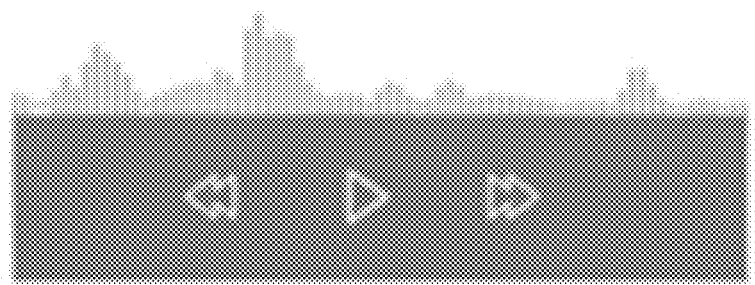

Referring to FIG. 10, a reaction test is based on sound and touching the screen by the injured. For example, referring to FIG. 10, the trainer will be instructed to hand the phone to the athlete. The athlete will be instructed to press the button that appears on the mobile device's screen each time he or she hears number '7'. The mobile app system will register the reaction delay (the time between number "7" and the button press) and this will contribute to the athlete's reaction score. The reaction time score will be computed based on the universal baseline and individual baseline. The mean, medium, and variance. In addition, a linear fitting will be applied to the response time in regard to the presentation number. The slope will indicate whether the response time is stable, faster, or slower in the process.

For example, an evaluator may start a reaction test. An injured is given a series of questions which the injured has to answer as quickly as possible. The proportion of correct answers is calculated into a percentage score and time to respond is also recorded. In a parallel path, reaction speed and using the mobile devices' accelerometer and touch screen to assess how quickly a user presses the screen after being audibly prompted can be used to determine a slow or quick response time.

Final Score and Individual Scores

After all tasks are finished, the mobile app or the concussion software stored on the server in some embodiments displays an overall weighted score indicating likelihood of concussion and suggests actions (play, sit out, consult with a doctor, and see a doctor right away). In addition, the four group scores will also display on buttons (cognition test, eye-tracking test, balance test, and reaction time test). When pressing on the buttons, detailed results will be shown and the ones that have low scores will be highlighted. If further pressed, the audio can be played.

The mobile device and the server each include a processor, memory, networking units that couple the mobile device and the server to networks, such as telephone and data networks. The mobile device and back end server are also each coupled to each other to exchange data. The memory stores program instructions for the respective concussion application program and back end functionality including data storage, analysis and scoring. The processor executes the program instructions to implement the software and method described herein. The mobile device may also include a camera, an accelerometer, a microphone, a touchscreen and other devices which produce data or a real time stream of data that are used in the concussion testing.

While particular embodiments of the present invention have been shown and described. A person having ordinary skill in the art will understand that changes may be made to those embodiments without departing from the spirit and scope of the present invention.

TABLE 2

| SCAT 3 Protocol |
|---|
| 1. GLASGOW COMA SCALE -the examiner should choose the most appropriate response based on evaluation. |
| * |
| Best Eye Response (E) |
| Eye opening in response to pain |
| Eye opening to speech |
| Eyes opening spontaneously |
| * |
| Best Verbal Response (V) |
| No verbal response |
| Incomprehensible sounds |
| Inappropriate words |
| Oriented |
| * |
| Best Motor Response (M) |
| No motor response |
| Extension to pain |
| Abnormal flexion to pain |
| Flexion/Withdrawal to pain |
| Localizes to pain |
| Obeys commands |
| 2. MADDOCKS SCORE- Examiner checks off 'yes or no' |
| "I am going to ask you a few questions, please listen carefully and give your best effort." |
| What venue are we at today? |
| Which half is it now? |
| Who scored last in this match? |
| What team did you play last week/game? |
| Did your team win the last game? |
| Notes can be record here using speech to text transcription, examiner will ask "tell me what happened?" |
| 3. HOW DO YOU FEEL? |
| Examiner will ask the athlete 22 symptoms questions. Examiner will manually choose a number from 0 to 6 on how severe the symptoms are (6 being most severe). |
| 4. COGNITIVE ASSESSMENT |
| Using speech recognition |
| * |
| Orientation |
| What month is it? |
| What is the date today? |
| What is the day of the week? |
| What year is it? |
| What time is it right now? (within 1 hour) |
| Immediate Memory: Repeat the following words: elbow, apple, carpet, saddle, carpet, bubble. |
| Concentration: Repeat the following in reverse order: |
| 1.      4-9-3 |
| 2.      3-8-1-4 |
| 3.      6-2-9-7-1 |
| 4.      7-1-8-4-6-2 |
| 5. "Tell me the months of year in reverse order starting with December.?" |

TABLE 2-continued

SCAT 3 Protocol

5. NECK EXAMINATION- Athlete is instructed to perform certain neck movements. Examiner can take notes. Speech to text transcription is used here with manual edit.
6. BALANCE EXAMINATION: user is to balance exercises as listed below. Using video analysis, errors are recorded by video.
Modified Balance Error Scoring System (BESS) testing
This balance testing is based on a modified version of the Balance Error Scoring System (BESS). A stopwatch or watch with a second hand is required for this testing.
Which foot was tested (i.e. which is the non-dominant foot) Left Right Testing Surface
"I am now going to test your balance. Please take your shoes off, roll up your pant legs above ankle (if applicable), and remove any ankle taping (if applicable). This test will consist of three twenty second tests with different stances"

(a) Double leg stance: "The first stance is standing with your feet together with your hands on your hips and with your eyes closed. You should try to maintain stability in that position for 20 seconds. I will be counting the number of times you move out of this position. I will start timing when you are set and have closed your eyes"

(b) Single leg stance: "If you were to kick a ball, which foot would you use? [This will be the dominant foot] Now stand on your non-dominant foot. The dominant leg should be held in approximately 30 degrees of hip flexion and 45 degrees of knee flexion. Again, you should try to maintain stability for 20 seconds with your hands on your hips and your eyes closed. I will be counting the number of times you move out of this position. If you stumble out of this position, open your eyes and return to the start position and continue balancing. I will start timing when you are set and have closed your eyes"

(c) Tandem stance: "Now stand heel-to-toe with your non-dominant foot in back. Your weight should be evenly distributed across both feet. Again, you should try to maintain stability for 20 seconds with your hands on your hips and your eyes closed. I will be counting the number of times you move out of this position. If you stumble out of this position, open your eyes and return to the start position and continue balancing. I will start timing when you are set and have closed your eyes.

And/or Tandem Gate
Participants are instructed to stand with their feet together behind a starting line (the test is best done with footwear removed). Then, they walk in a forward direction as quickly and as accurately as possible along a 38 mm wide (sports tape), 3 meter line with an alternate foot heel-to-toe gait ensuring that they approximate their heel and toe on each step. Once they cross the end of the 3 m line, they turn 180 degrees and return to the starting point using the same gait. A total of 4 trials are done and the best time is retained. Athletes should complete the test in 14 seconds. Athletes fail the test if they step off the line, have a separation between their heel and toe, or if they touch or grab the examiner or an object. In this case, the time is not recorded and the trial repeated, if appropriate.
Balance Testing - types of errors
    Hands lifted off iliac crest
    Opening eyes
    Step, stumble or fall
    Moving hip into >30 degrees abduction
    Lifting forefoot or heel
    Remaining out of test position >5 sec
Each of the 20-second trials is scored by counting the errors, or deviations from the proper stance, accumulated by the athlete. The examiner will begin counting errors only after the individual has assumed the proper start position. The modified BESS is calculated by adding one error point for each error during the three 20-second tests. The maximum total number of errors for any single condition is 10. Subjects that are unable to maintain the testing procedure for a minimum of five seconds at the start are assigned the highest possible score, ten, for that testing condition.
Double Leg Stance (feet together)
Single Leg Stance (non-dominant foot)
Tandem Stance (non-dominant foot at back)
Balance Examination score (30 score total errors)
And/or Tandem gait:
7. COORDINATION
Finger-to-nose (FTN) task: using video analysis
"I am going to test your coordination now. Please sit comfortably on the chair with your eyes open and your arm (either right or left) outstretched (shoulder flexed to 90 degrees and elbow and fingers extended). When I give a start signal, I would like you to perform five successive finger to nose repetitions using your index finger to touch the tip of the nose as quickly and as accurately as possible."
Which arm was tested: Left Right Scoring: 5 correct repetitions in <4 seconds = 1
Note for testers: Athletes fail the test if they do not touch their nose, do not fully extend their elbow or do not perform five repetitions. Failure should be scored as 0.
8. DELAYED RECALL
"Do you remember that list of words I read a few times earlier? Tell me as many words from the list as you can remember in any order."
Speech recognition is used to capture response.
* * *

What is claimed is:

1. A method for determining whether a user has a concussion, comprising:
    using a mobile device to interact with a user using a display, cameras, the speakers and a microphone to follow a concussion protocol;
    collecting audio in response to specific questions from the user using the microphone; and
    recognizing speech using automatic speech recognition (ASR);
    determining whether the responses to the questions are correct based on the ASR responses to the questions and predetermined answers stored on the mobile device or a back end server;
    determining whether the ASR responses have differences in delay or pitch from prior versions of the ASR responses for the user stored in connection with the concussion protocol for the user;
    determining a score for the user based on the ASR responses and the differences; and
    providing the score and concussion protocol testing data to the user or a medical service provider.

2. The method according to claim 1, further comprising:
    filming the user's eyes following a camera associated with the mobile device; and
    analyzing the user's eye movement to determine a score for eye tracking;
    using the eye tracking analysis as a component of the score.

3. The method according to claim 1, further comprising:
    analyzing the user's movement and reactions using the mobile device; and
    determining the score based in part on the analyzed movement and reactions.

* * * * *